US007597090B2

(12) United States Patent
Hashimoto et al.

(10) Patent No.: US 7,597,090 B2

(45) Date of Patent: Oct. 6, 2009

(54) INTERNAL COMBUSTION ENGINE

(75) Inventors: Kohtaro Hashimoto, Wako (JP); Kohjiroh Aimoto, Wako (JP); Takahiro Gunji, Wako (JP); Fumiaki Ikegawa, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 380 days.

(21) Appl. No.: 11/716,557

(22) Filed: Mar. 12, 2007

(65) Prior Publication Data

US 2007/0215098 A1 Sep. 20, 2007

(30) Foreign Application Priority Data

Mar. 15, 2006 (JP) ............................ 2006-071355

(51) Int. Cl.
*F02B 13/00* (2006.01)
*C07C 45/00* (2006.01)

(52) U.S. Cl. ...................... 123/575; 123/295; 123/577; 568/357

(58) Field of Classification Search ..................... 123/3, 123/295, 304, 305, 431, 478, 480, 575, 577; 701/104, 105; 568/357, 399, 910
See application file for complete search history.

(56) References Cited

U.S. PATENT DOCUMENTS

2008/0044709 A1* 2/2008 Ito .............................. 429/33
2008/0050631 A1* 2/2008 Ito et al. ....................... 429/29

FOREIGN PATENT DOCUMENTS

JP 2004-308423 A 11/2004

* cited by examiner

*Primary Examiner*—John T Kwon
(74) *Attorney, Agent, or Firm*—Birch, Stewart, Kolasch & Birch, LLP

(57) ABSTRACT

The present invention provides an internal combustion engine which can produce several types of fuels from a single fuel as needed. The internal combustion engine comprises reforming means 3 for reforming a first fuel to be used in homogeneous charge compression ignition combustion into a second fuel having high ignitability, by making the first fuel contact with a catalyst formed from N-hydroxyphthalimide. The engine uses the second fuel when conducting diesel combustion. The engine can switch between the homogeneous charge compression ignition combustion with the use of the first fuel and the diesel combustion with the use of the second fuel. The engine conducts the homogeneous charge compression ignition combustion when a load is low, and conducts the diesel combustion when the load is high. The internal combustion engine further comprises a first fuel injector **4*b* which injects the first fuel to an air intake port when the homogeneous charge compression ignition combustion is conducted, and a second fuel injector 4*a* which directly injects the second fuel to a combustion chamber when the diesel combustion is conducted. The engine further comprises fuel injection timing control means 7** for switching between the homogeneous charge compression ignition combustion and the diesel combustion, by changing the injection timing of the fuel. The first fuel is at least one of gasoline, kerosene, light oil and alcohol.

7 Claims, 1 Drawing Sheet

INTERNAL COMBUSTION ENGINE

BACKGROUND OF THE INVENTION

1. Field of the Invention

The present invention relates to an internal combustion engine which uses several types of fuels.

2. Description of the Related Art

In recent years, in order to improve a fuel efficiency and reduce emission of an internal combustion engine, a compression ignition internal combustion engine represented by a homogeneous charge compression ignition internal combustion engine has been studied. The homogeneous charge compression ignition internal combustion engine compresses a fuel-air mixture consisting of fuel and air in a combustion chamber of the internal combustion engine to self-ignite the fuel-air mixture.

However, the homogeneous charge compression ignition internal combustion engine has a problem that the engine has a narrow stably-operatable region, because knocking easily occurs when a high load is required to the engine, and misfire easily occurs when a low load is required to the engine.

In order to solve the problem, an internal combustion engine using several types of fuels is proposed. For instance, the internal combustion engine is known which switches between homogeneous charge compression ignition combustion with the use of light oil and gasoline, and diesel combustion with the use of only the light oil, according to an operating state of the internal combustion engine (cf. Japanese Patent Laid-Open No. 2004-308423).

However, the internal combustion engine has such an inconvenience as to need to prepare each independent fuel tank and fuel supply system, because of using two types of fuels, namely, light oil and gasoline.

SUMMARY OF THE INVENTION

An object of the present invention is to provide an internal combustion engine which can produce several types of fuels from a single fuel as needed, so as to dissolve the above inconvenience.

In order to achieve the above object, the present invention provides an internal combustion engine comprising a reforming means for reforming a first fuel to be used in homogeneous charge compression ignition combustion into a second fuel having higher ignitability than the first fuel, by making the first fuel contact with a catalyst formed from N-hydroxyphthalimide.

The internal combustion engine according to the present invention can reform the first fuel to the second fuel having higher ignitability than the first fuel, through the reforming means. In other words, the internal combustion engine according to the present invention can prepare the two fuels of the first fuel and the second fuel having different ignitability from each other, from the first fuel. Accordingly, by appropriately using both of the fuels, the internal combustion engine can be stably operated for a wide range of a load.

The internal combustion engine according to the present invention can conduct diesel combustion with the use of the second fuel. Light oil is generally used for the diesel combustion. However, because the internal combustion engine according to the present invention can produce the second fuel having higher ignitability than the first fuel, through the reforming means, the internal combustion engine can use various fuels having low ignitability for the diesel combustion.

It is preferable that the internal combustion engine according to the present invention can switch between the homogeneous charge compression ignition combustion with the use of the first fuel and the diesel combustion with the use of the second fuel. The homogeneous charge compression ignition combustion is conducted when a load is low, and the diesel combustion is conducted when the load is high.

The internal combustion engine according to the present invention preferably has a first fuel injector which injects the first fuel to an air intake port when the engine conducts the homogeneous charge compression ignition combustion, and a second fuel injector which directly injects the second fuel to a combustion chamber when the engine conducts the diesel combustion, so as to enable the engine to switch between the homogeneous charge compression ignition combustion with the use of the first fuel and the diesel combustion with the use of the second fuel.

The internal combustion engine according to the present invention also preferably has a fuel injection timing control means for switching between the homogeneous charge compression ignition combustion and the diesel combustion, by changing the injection timing of the fuel. Specifically, the fuel injection timing control means forms fuel-air mixture in a combustion chamber when the engine conducts the homogeneous charge compression ignition combustion, by injecting the first fuel into the combustion chamber before the air is compressed therein; and when the engine conducts the diesel combustion, the fuel injection timing control means injects the second fuel when the air in the combustion chamber is compressed to reach a high temperature.

The internal combustion engine according to the present invention can employ at least one fuel selected from the group consisting of gasoline, kerosene, light oil and alcohol, as the first fuel.

DETAILED DESCRIPTION OF THE PREFERRED EMBODIMENTS

In the next place, preferred embodiments according to the present invention will be described in further detail with reference to the attached drawings.

Figure 1:
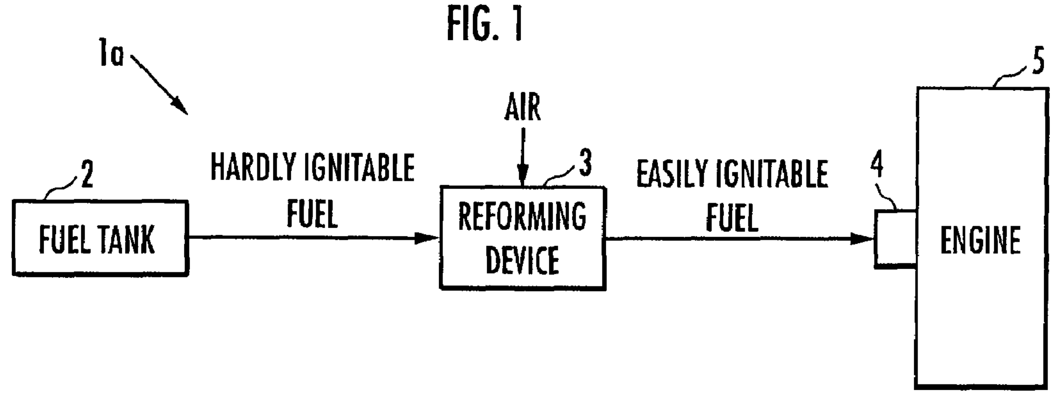
FIG. 1 is a system block diagram showing one embodiment of an internal combustion engine according to the present invention.

As shown in FIG. 1, a first internal combustion engine 1*a* according to the present embodiment has: a fuel tank 2 for accommodating a first fuel (hardly ignitable fuel) to be used in homogeneous charge compression ignition combustion: a reforming device 3 for reforming the fuel supplied from the fuel tank 2 to the second fuel (easily ignitable fuel) having higher ignitability than the first fuel; and an engine 5 which conducts diesel combustion with the use of the second fuel supplied through an injector 4.

The first fuel stored in the fuel tank 2 is a fuel such as gasoline, kerosene, light oil and alcohol, which may be single or plurally mixed.

The reforming device 3 accommodates a catalyst formed from N-hydroxyphthalimide, and reforms the first fuel to the second fuel having higher ignitability than the first fuel, by making the first fuel contact with the catalyst. In the next place, a mechanism through which N-hydroxyphthalimide reforms the first fuel will be described, while taking hydrocarbon such as gasoline and kerosene as an example of the first fuel.

As shown in the following reaction formula (1), N-hydroxyphthalimide firstly reacts with oxygen in the air, and is changed to a phthalimido-N-oxyl radical. Next, as shown in the reaction formula (2), the phthalimido-N-oxyl radical abstracts hydrogen of hydrocarbon (RH) to be reduced into N-hydroxyphthalimide by itself on one hand, and produces hydrocarbon radical (R.) on the other hand.

Subsequently as shown in the reaction formula (3), the hydrocarbon radical (R.) is oxidized by oxygen in the air, and is converted to a peroxide radical (ROO.) of hydrocarbon. Then, as shown in the reaction formula (4), the peroxide radical (ROO.) of hydrocarbon abstracts hydrogen of hydrocarbon (RH) to be changed into hydroperoxide (ROOH), and simultaneously produces a hydrocarbon radical (R.).

(1)

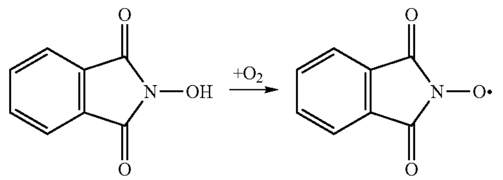

(2)

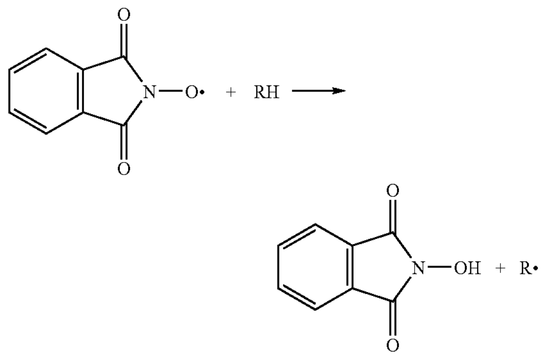

(3)

$$R\cdot + O_2 \longrightarrow ROO\cdot$$

(4)

$$ROO\cdot + RH \longrightarrow ROOH + R\cdot$$

The reaction formulas (3) and (4) are a chain reaction, so that the first fuel formed from hydrocarbon such as gasoline and kerosene is automatically oxidized, and hydroperoxide (ROOH) having higher ignitability than hydrocarbon (RH) is produced in the first fuel. As a result of this, the second fuel having higher ignitability than the first fuel is obtained.

The reactions in the reaction formulas (1) to (4) occur in the hydrocarbon taken as an example, but similar reactions also occur when alcohol (ROH) is used instead of hydrocarbon. In the case of alcohol (ROH), HOR. is produced instead of R. in the reaction formula (2), and RO. is oxidized to produce HOROO. in the reaction formula (3). Then, HOROO. abstracts hydrogen of an alkyl group (R) in the alcohol (ROH) in the reaction formula (4) to be changed into hydroperoxide (ROOH) and simultaneously produce HOR..

It is preferable for the reactions in the reaction formulas (1) to (4) to proceed at about 80° C. Exhaust gas of an engine 5, for instance, can be used as a heat source.

In the next place, an example will be shown in which kerosene as the first fuel is automatically oxidized by N-hydroxyphthalimide.

At first, 1 g or 10 g of N-hydroxyphthalimide as a catalyst was mixed with 100 g of kerosene, and the mixture was held at 80° C. for one hour while air was blown into the mixture. Next, the reacted solution was cooled down to room temperature, and was filtrated to remove N-hydroxyphthalimide. Thus, a second fuel was obtained as the filtrate.

Subsequently, the ignitability of light oil, kerosene and the second fuel was evaluated. The ignitability was evaluated by using an atomization ignition testing instrument (Trade name: FIA-100 made by Fueltech AS.), injecting the fuel into the combustion chamber in a temperature of 500° C. and a pressure of 2 MPa, and measuring a period of time spent for the pressure in the combustion chamber to increase by 0.02 MPa after the fuel was injected, which is referred to as an ignition delay time. An average of ten measurement values is shown in Table 1.

TABLE 1

| | Ignition delay time (ms) |
|---|---|
| First fuel (kerosene) | 6.35 |
| Second fuel (catalyst 1 g) | 5.82 |
| Second fuel (catalyst 10 g) | 5.18 |
| Light oil | 4.97 |

It is clear from table 1 that a second fuel obtained by making kerosene as the first fuel contact with N-hydroxyphthalimide to automatically oxidize the kerosene has shorter ignition delay time than that of kerosene as the first fuel, namely, has higher ignitability. The second fuel also shows a tendency of approaching to the ignitability of light oil along with the increase of a catalyst amount, so that it is clear that the second fuel can be used for diesel combustion.

Figure 2:
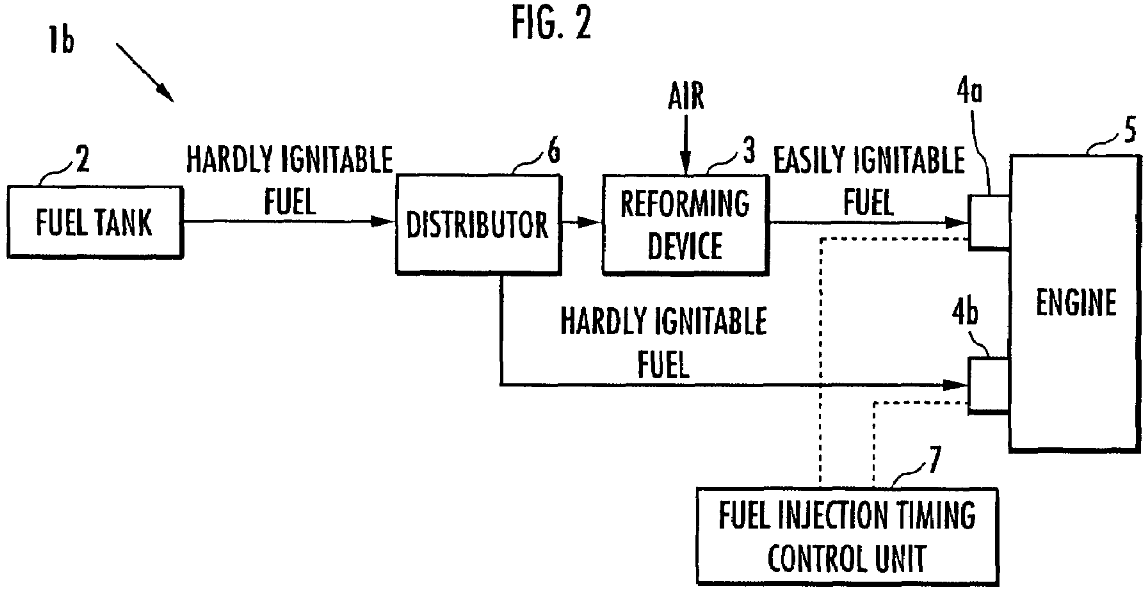
FIG. 2 is a system block diagram showing another embodiment of an internal combustion engine according to the present invention.

In the next place, a second internal combustion engine **1*b* according to the present embodiment will be described with reference to FIG. 2. The internal combustion engine 1*b* has: a fuel tank 2 for accommodating the first fuel (hardly ignitable fuel) to be used for homogeneous charge compression ignition combustion; a reforming device 3 for reforming the fuel supplied from the fuel tank 2 to the second fuel (easily ignitable fuel) having higher ignitability than the first fuel; an engine 5 for conducting diesel combustion with the use of the second fuel supplied through an injector 4*a*; and a distributor 6 made of a cross valve placed between the fuel tank 2 and the reforming device 3 so that the first fuel accommodated in the fuel tank 2 can be directly supplied to the engine 5 without passing the reforming device 3 but through an injector 4*b***.

The injector **4*a* directly injects the second fuel to a combustion chamber of the engine 5, and the injector 4*b* injects the first fuel to an air intake port of the engine 5. The internal combustion engine 1*b* also has a fuel injection timing control unit 7 for controlling the fuel injection timing of the injectors 4*a* and 4*b***.

Because of having the distributor 6, the internal combustion engine **1*b* can use two fuels of a first fuel accommodated in a fuel tank 2 and a second fuel which has been reformed from the first fuel by the reforming device 3 as described above and has higher ignitability than the first fuel. Then, the internal combustion engine 1*b* injects the first fuel from the injector 4*b* to the air intake port of the engine 5 before air in the combustion chamber is compressed, when a load is low, produces a fuel-air mixture in the combustion chamber, and conducts homogeneous charge compression ignition combustion with the use of the fuel-air mixture. On the other hand, when the load is high, the internal combustion engine 1*b* directly injects the second fuel from the injector 4*a* to the combustion chamber of the engine 5 when the air in the combustion chamber is compressed to reach a high temperature, and conducts diesel combustion. The fuel injection timing control unit 7 changes the fuel injection timing for the first fuel and the second fuel to switch between the homogeneous charge compression ignition combustion and the diesel combustion, in the internal combustion engine 1***b*.

The internal combustion engine 1*b* can be stably operated for a wide range of a load by appropriately using two fuels of the first fuel and the second fuel having different ignitability from each other.

What is claimed is:

1. An internal combustion engine comprising a reforming means for reforming a first fuel to be used in homogeneous charge compression ignition combustion into a second fuel having higher ignitability than the first fuel, by making the first fuel contact with a catalyst formed from N-hydroxyphthalimide.

2. The internal combustion engine according to claim 1, further comprising conducting diesel combustion with the use of the second fuel.

3. The internal combustion engine according to claim 1, wherein the internal combustion engine is switchable between the homogeneous charge compression ignition combustion with the use of the first fuel and the diesel combustion with the use of the second fuel.

4. The internal combustion engine according to claim 3, further comprising conducting the homogeneous charge compression ignition combustion when a load is low, and conducting the diesel combustion when the load is high.

5. The internal combustion engine according to claim 3, further comprising a first fuel injector which injects the first fuel to an air intake port when the homogeneous charge compression ignition combustion is conducted, and a second fuel injector which directly injects the second fuel to a combustion chamber when the diesel combustion is conducted.

6. The internal combustion engine according to claim 3, further comprising a fuel injection timing control means for switching between the homogeneous charge compression ignition combustion and the diesel combustion, by changing the injection timing of the fuel.

7. The internal combustion engine according to claim 1, wherein the first fuel is at least one type of fuel selected from the group consisting of gasoline, kerosene, light oil and alcohol.

* * * * *